United States Patent [19]
Ahr et al.

[11] Patent Number: 5,788,686
[45] Date of Patent: Aug. 4, 1998

[54] ABSORBENT ARTICLE HAVING A COVERSHEET WITH EXTENDIBLE FLAPS

[75] Inventors: Nick A. Ahr; Patricia L. Christon, both of Cincinnati; Allison K. Hunter, West Chester, all of Ohio

[73] Assignee: The Procter & Gamble Company, Cincinnati, Ohio

[21] Appl. No.: 638,687

[22] Filed: Apr. 26, 1996

Related U.S. Application Data

[63] Continuation of Ser. No. 234,321, Apr. 28, 1994, abandoned.

[51] Int. Cl.⁶ ............................................. A61F 13/15
[52] U.S. Cl. .................... 604/389; 604/387; 604/385.1
[58] Field of Search ......................... 604/358, 385.1, 604/385.2, 386, 389–391, 398; 206/440

[56] References Cited

U.S. PATENT DOCUMENTS

| | | | |
|---|---|---|---|
| 2,693,806 | 11/1954 | Wright | 128/286 |
| 2,929,379 | 3/1960 | Poulsen | 128/290 |
| 3,367,334 | 2/1968 | Testa | 128/290 |
| 3,397,697 | 8/1968 | Rickard | 128/288 |
| 3,570,492 | 3/1971 | Bettencourt | 128/290 |
| 3,913,580 | 10/1975 | Ginocchio | 128/290 |
| 4,186,743 | 2/1980 | Steiger | 128/284 |
| 4,285,343 | 8/1981 | McNair | 128/287 |
| 4,405,310 | 9/1983 | Karami | 604/383 |
| 4,425,130 | 1/1984 | DesMarais | 604/389 |
| 4,536,181 | 8/1985 | Cook | 604/387 |
| 4,576,597 | 3/1986 | Hlaban | 604/390 |
| 4,589,876 | 5/1986 | Van Tilburg | 604/385 |
| 4,596,570 | 6/1986 | Jackson et al. | 604/387 |
| 4,597,759 | 7/1986 | Johnson | 604/385 |
| 4,701,178 | 10/1987 | Glaug et al. | 604/387 |
| 4,759,754 | 7/1988 | Korpman | 604/387 |
| 4,773,905 | 9/1988 | Molee et al. | 604/378 |
| 5,009,653 | 4/1991 | Osborn, III | 604/385.1 |
| 5,125,918 | 6/1992 | Seidy | 604/386 |
| 5,133,704 | 7/1992 | Wheeler | 604/387 |
| 5,133,705 | 7/1992 | Nakanishi et al. | 604/387 |
| 5,201,727 | 4/1993 | Nakanishi et al. | 604/390 |
| 5,221,275 | 6/1993 | Van Iten | 604/387 |
| 5,275,591 | 1/1994 | Mavinkurve | 604/387 |
| 5,281,209 | 1/1994 | Osborn, III | 604/385.1 |
| 5,330,461 | 7/1994 | Leeker | 604/385.1 |
| 5,342,342 | 8/1994 | Kitaoka | 604/385.2 |

FOREIGN PATENT DOCUMENTS

| | | |
|---|---|---|
| 0 347 319 B1 | 1/1993 | European Pat. Off. . |
| 2 374 890 | 12/1976 | France .................. A61F 13/16 |
| 2244653 | 11/1991 | United Kingdom ............. 604/398 |
| WO 89/02729 | 4/1989 | WIPO . |
| WO 92/18080 | 10/1992 | WIPO ..................... A61F 13/58 |

*Primary Examiner*—Robert A. Clarke
*Assistant Examiner*—Dennis Ruhl
*Attorney, Agent, or Firm*—Kevin C. Johnson; Roddy M. Bullock; Jacobus C. Rasser

[57] ABSTRACT

The present invention pertains to an absorbent article. The absorbent article includes a topsheet, a backsheet joined to the topsheet and an absorbent core positioned between the topsheet and the backsheet. A coversheet is joined to the topsheet. The coversheet includes a line of weakness defining a flap to be at least partially separated from the remainder of the coversheet.

6 Claims, 3 Drawing Sheets

ABSORBENT ARTICLE HAVING A COVERSHEET WITH EXTENDIBLE FLAPS

This is a continuation of application Ser. No. 08/234,321, filed on Apr. 28, 1994 now abandoned.

TECHNICAL FIELD

The present invention relates to absorbent articles, and more particularly, the present invention relates to absorbent articles having a coversheet with integral, extendible flaps.

BACKGROUND OF THE INVENTION

All manner and variety of absorbent articles configured for the absorption of bodily fluids are, of course, well-known. Current types of absorbent articles include sanitary napkins, pantiliners, disposable diapers, absorbent bandages, and incontinent briefs.

Sanitary napkins having flaps extending from the longitudinal edges of the central absorbent pad are known in the art. The flaps may comprise a liquid pervious topsheet, a liquid impervious backsheet joined to the topsheet, and an absorbent core positioned between the topsheet and the backsheet. The flaps may be folded over onto either the topsheet or the backsheet of the sanitary napkin prior to use. In use, the user unfolds the flaps and wraps them about the crotch portion of the panty where the flaps are secured to the panty by means of an adhesive.

SUMMARY OF THE INVENTION

The present invention pertains, in a preferred embodiment, to an absorbent article including a topsheet having a body facing surface and a garment facing surface, a backsheet joined to said garment facing surface of said topsheet, and an absorbent core positioned between said topsheet and said backsheet. The absorbent article comprises a coversheet joined to the body facing surface of the topsheet. The coversheet includes a line of weakness defining at least one flap to be at least partially separated from the remainder of the coversheet. Preferably, the line of weakness is substantially continuous and includes perforations.

The coversheet preferably includes a pair of flaps. The flaps are preferably liquid impervious. The exposed surface of the flaps includes a fastening adhesive.

Preferably, the periphery of the coversheet is joined to the body facing surface of said topsheet along its periphery.

In another preferred embodiment the absorbent article has a longitudinal centerline and a transverse centerline. The flaps may be extendible in a direction substantially parallel to the transverse centerline of said absorbent article upon being partially separated from the remainder of said coversheet. Alternatively, the flaps may be extendible in a direction substantially parallel to the longitudinal centerline of said absorbent article upon being separated from the remainder of said coversheet.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
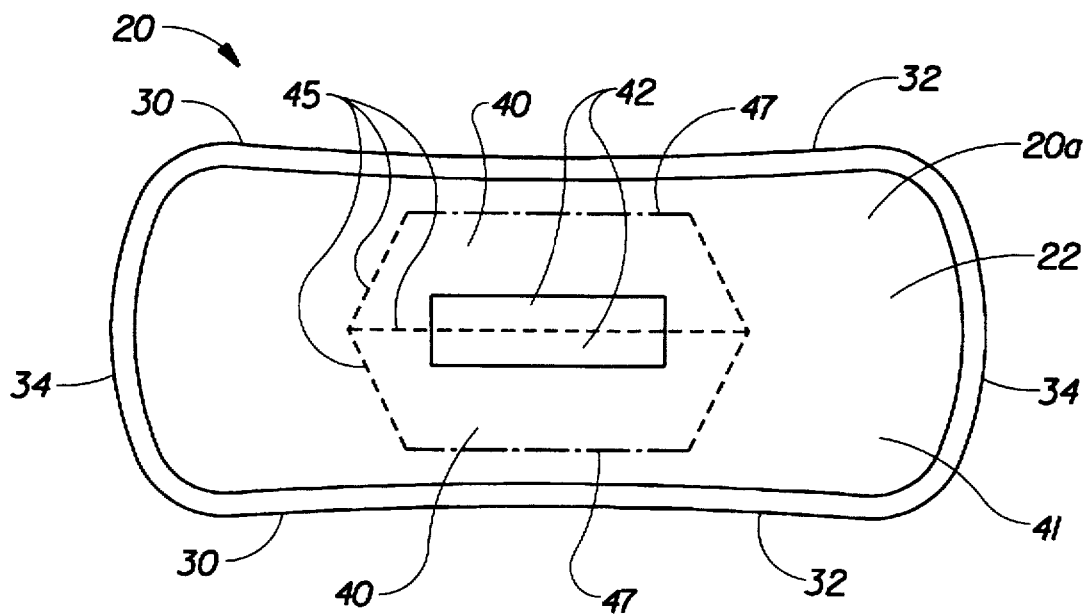
FIG. 1 is a top plan view of a sanitary napkin embodiment of the present invention.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

Figure 2:
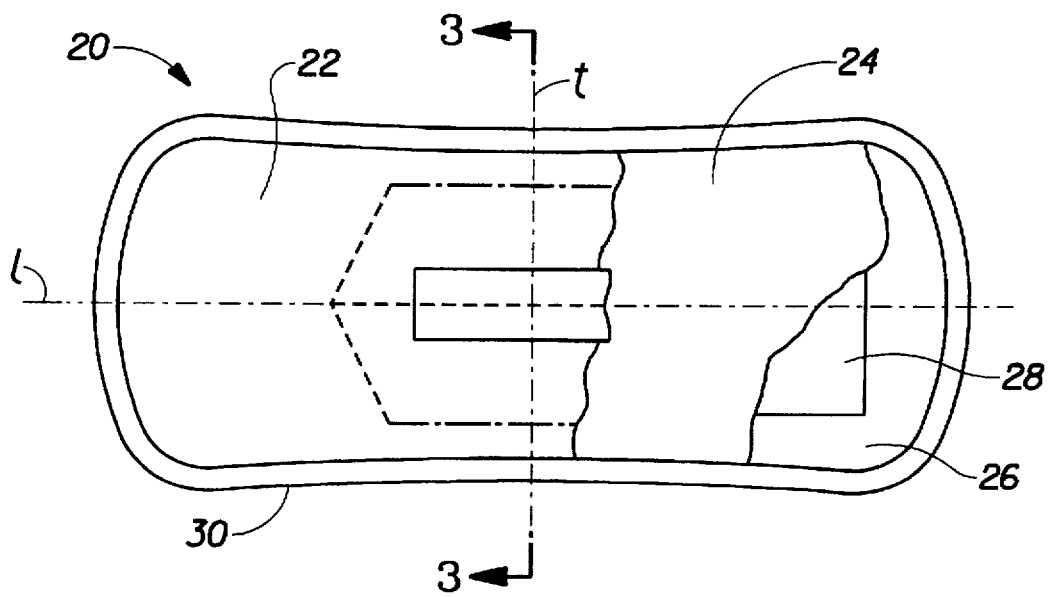
FIG. 2 is a top plan view of the sanitary napkin of FIG. 1 with portions of the sanitary napkin cut-away to more clearly show the construction of the sanitary napkin.

The sanitary napkin 20 has two surfaces, a body-contacting surface or "body surface" 20a and a garment surface 20b. The sanitary napkin 20 is shown in FIGS. 1 and 2 as viewed from its body surface 20a. The body surface is intended to be worn adjacent to the body of the wearer while the garment surface is on the opposite side and is intended to be placed adjacent to the wearer's undergarments when the sanitary napkin 20 is worn.

FIG. 1 also shows that the sanitary napkin 20 has a periphery 30 which is defined by the outer edges of the sanitary napkin 20 in which the longitudinal edges are designated 32 and the end edges are designated 34.

FIG. 2 is a plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 2, the sanitary napkin 20 preferably comprises a coversheet 22, a liquid pervious topsheet 24, a liquid impervious backsheet 26 joined with the topsheet 24, and an absorbent core 28 positioned between the topsheet 24 and the backsheet 26.

FIG. 2 shows a preferred embodiment of the sanitary napkin 20 in which the topsheet 24 and the first backsheet 26 have length and width dimensions generally larger than those of the absorbent core 28. The topsheet 24 and the backsheet 26 extend beyond the edges of the absorbent core 28 to form portions of the periphery 30.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

Figure 3:
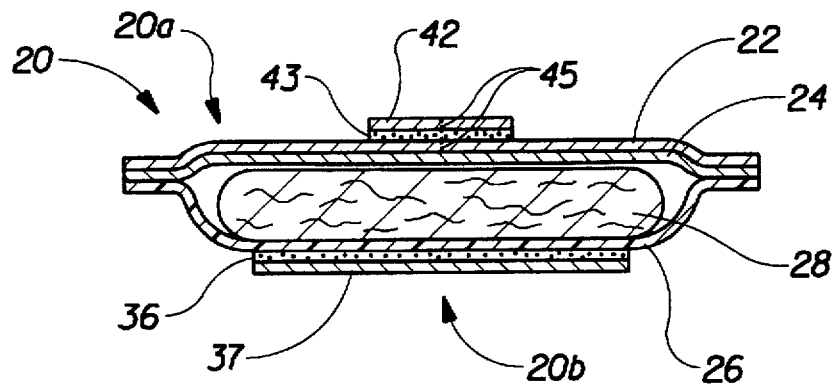
FIG. 3 is a cross-sectional view of the sanitary napkin of FIG. 2 taken along section line 3—3.

FIG. 3 is a cross-sectional view of the sanitary napkin 20 taken along section line 3—3 of FIG. 2. As can be seen in FIG. 3 the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

The absorbent core 28 may be any absorbent means which is capable of absorbing or retaining liquids (e.g., menses and/or urine). As shown in FIG. 2, the absorbent core 28 has a body surface, a garment surface, side edges, and pad edges.

The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to each other by attachment means (not shown) such as those well known in the art. For example, the backsheet 26 and/or the topsheet 24 may be secured to the absorbent core 28 or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986 issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheets may permit vapors to escape from the absorbent core 28 (i.e., breathable) while still preventing exudates from passing through the backsheet.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

In use, the sanitary napkin 20 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer surface of the backsheet 26 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/0 both of which are manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, an acquisition layer(s) may be positioned between the topsheet and the absorbent core. The acquisition layer may serve several functions including improving wicking of exudates over and into the absorbent core. There are several reasons why the improved wicking of exudates is important, including providing a more even distribution of the exudates throughout the absorbent core and allowing the sanitary napkin 20 to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. Each of these references are incorporated herein by reference. In a preferred embodiment, the acquisition layer may be joined with the topsheet by any of the conventional means for joining webs together, most preferably by fusion bonds as is more fully described in the above-referenced Cree application.

Referring now to FIGS. 1–3, the coversheet 22 is positioned adjacent the body surface of the topsheet 24. The coversheet preferably extends beyond the edges of the absorbent core 28 to form portions of the periphery 30. Coversheet 22 preferably includes integral flaps 40 which may be partially separated from the remaining portion of coversheet 22 along substantially continuous lines of weakness 45. In the illustrated embodiment of FIGS. 1–3, substantially continuous lines of weakness 45 comprise lines of perforations in coversheet 22. Flaps 40 of coversheet 22 are preferably liquid impervious and are preferably manufactured from a thin plastic film, although other flexible liquid impervious materials may also be used. The flaps 40 may comprise a woven or nonwoven material, polymeric films such as thermoplastic films of polyethylene or polypropylene, or composite materials such as a film-coated nonwoven material. The portion of coversheet 22 surrounding flaps 40 is generally designated as 41. Portion 41 may either be liquid impervious or liquid pervious. Portion 41 may be manufactured from a wide variety of materials such as those used for topsheet 24, backsheet 26, and flaps 40, as mentioned above.

Flaps 40 preferably include an adhesive fastening means 43 on their exposed surface for attaching the flaps to the undergarment of the wearer. Removable release liners 42 cover the adhesive fastening means 43 to keep the adhesive from sticking to a surface other than the crotch portion of the undergarment prior to use.

Alternatively, fold lines 47 may be replaced with a line of weakness. Thus, the user may remove the flaps 40 from the remaining portion of the coversheet 22. In this embodiment, the coversheet 22 will act as an overwrap for the topsheet prior to use, protecting the topsheet from the elements.

Prior to use, coversheet 22 acts as an overwrap for topsheet 24. Coversheet 22 thus prevents topsheet 24 from being exposed to the elements, e.g., dust and dirt, prior to use. Therefore, there is no need for an additional overwrap to protect topsheet 24.

Figure 4:
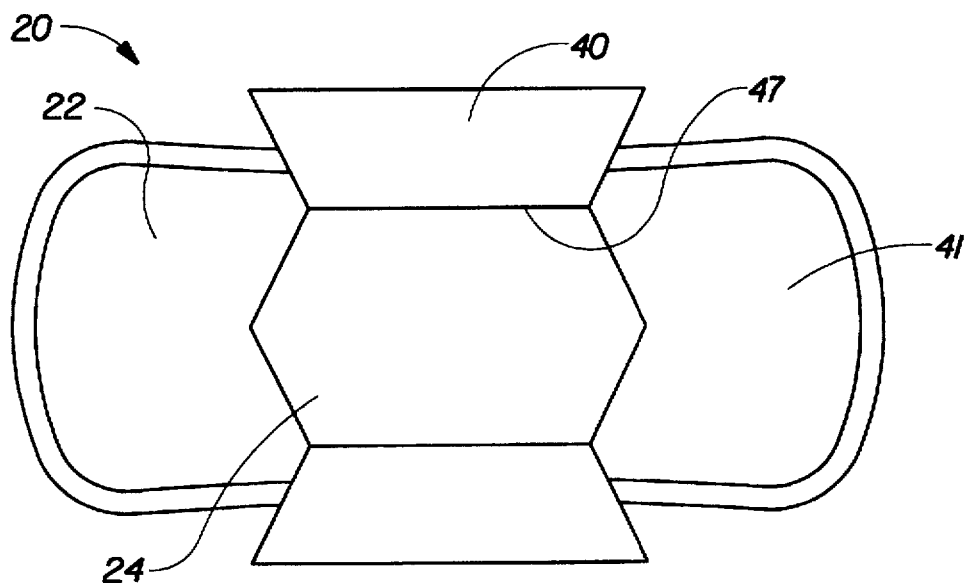
FIG. 4 is a top plan view of the sanitary napkin of FIGS. 1 and 2 with the flaps extended.

Referring now to FIG. 4, the sanitary napkin 20 is shown with the flaps 40 having been partially separated from coversheet 22 along lines of weakness 45 thus exposing topsheet 24. To partially separate the flaps 40 from the coversheet 22, the user pulls flaps 40 upward and away from the remaining portion of coversheet 22, thereby partially separating the flaps 40 from the remaining portions 41 of coversheet 22 along lines of weakness 45. The user then folds flaps 40 along fold lines 47 and attaches the flaps 40 to the underside of an undergarment by means of adhesive fastening means 43 which may be exposed upon by the removal of release liners 42.

Flaps 40 may be of essentially any shape, and may extend to the longitudinal edges 32 and the end edges 34. Flaps 40 provide additional protection against soiling of the undergarment.

Alternatively, fold line 47 may be replaced with a line of weakness allowing the user to completely remove the flaps 40 from the remaining portion 41 of the coversheet 22. The removable flaps will act as an overwrap protecting the topsheet from the elements prior to use.

Figure 5:
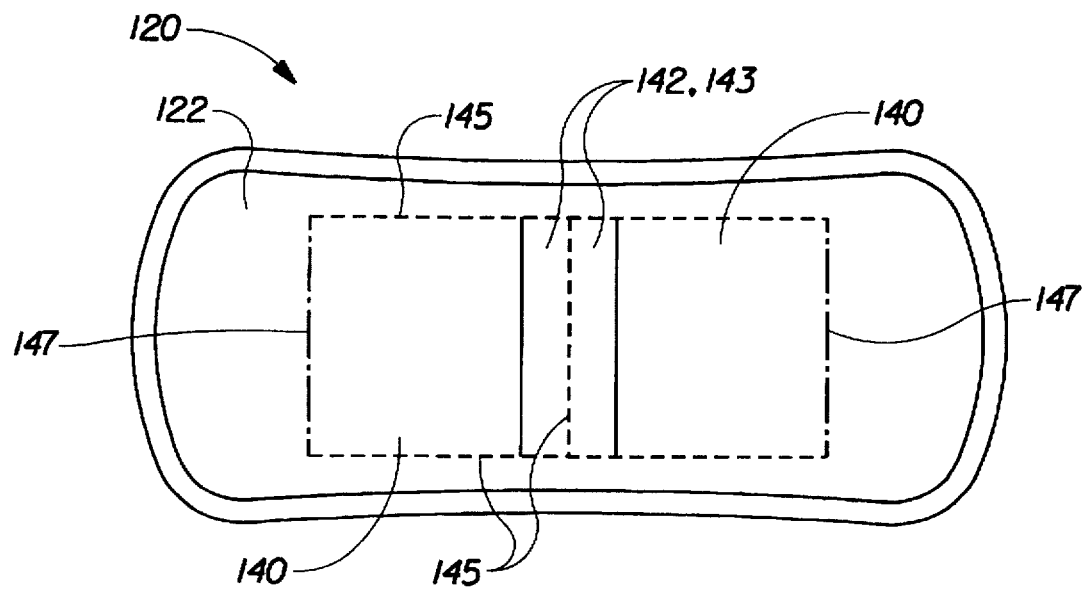
FIG. 5 is a top plan view of another sanitary napkin embodiment of the present invention.
Figure 6:
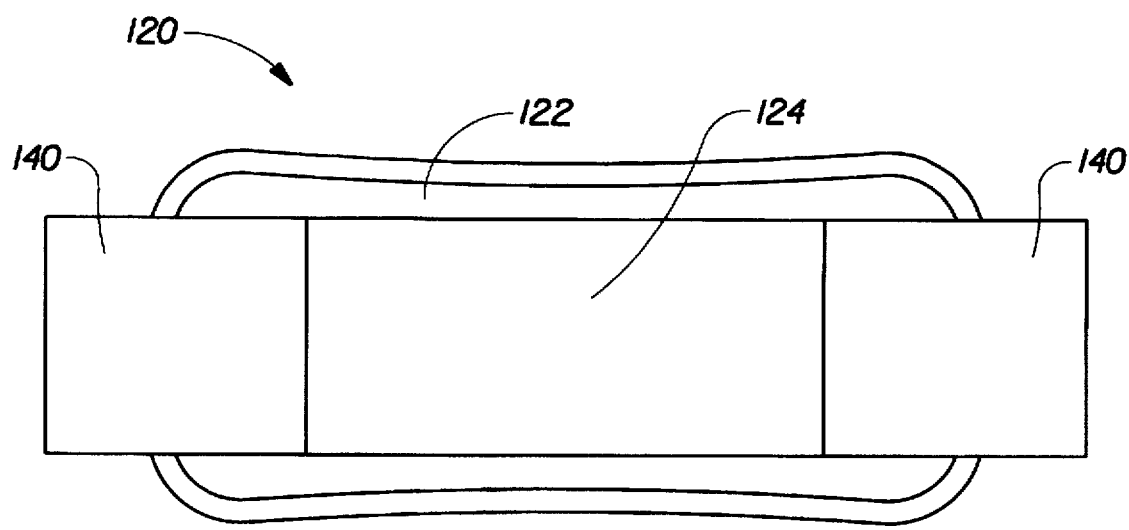
FIG. 6 is a top plan view of the sanitary napkin of FIG. 5 having the flaps fully extended.

In FIGS. 5 and 6 there is shown another preferred embodiment of a sanitary napkin 120 of the present invention. Sanitary napkin 120 includes a coversheet 122, a topsheet 124, and an absorbent core and a backsheet (not shown). Coversheet 122 includes a pair of integral flaps 140 partially separable from the remaining portion of coversheet 122 along lines of weakness 145. To partially separate flaps 140 from coversheet 122 the user lifts flaps 140 upward and away from the remaining portion of coversheet 122, thereby partially separating the flaps 140 from the remaining portion of coversheet 122 along lines of weakness 145. The user then folds flaps 140 along fold lines 147 and secures the flaps 140 to an undergarment by means of a panty fastening adhesive 143 which is exposed upon the removal of release liners 142. Upon separation of flaps 140, topsheet 124 is exposed.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article including a topsheet having a body facing surface and a garment facing surface, a backsheet joined to said garment facing surface of said topsheet, and an absorbent core positioned between said topsheet and said backsheet, said absorbent article having a longitudinal centerline and a transverse centerline, said absorbent article comprising:

(a) a coversheet joined to said body facing surface of said topsheet and forming a protective overwrap for said topsheet prior to use, said coversheet including a line of weakness completely surrounding and defining a pair of flaps and a remaining portion of said coversheet at least partially surrounding said flaps, said flaps being partially separable so as to expose at least a portion of said topsheet for use, said line of weakness being substantially continuous and including perforations, and wherein said flaps may be fully separated from said remaining portion of said coversheet along said line of weakness, wherein said flaps have an exposed surface facing away from said topsheet, said flaps including a fastening adhesive on their exposed surfaces for attaching said flaps to an undergarment.

2. The absorbent article of claim 1, wherein said flaps are liquid impervious.

3. The absorbent article of claim 1, wherein said coversheet includes a periphery, said coversheet being joined to said body facing surface of said topsheet along said periphery.

4. The absorbent article of claim 1, wherein said flaps are extendible in a direction substantially parallel to the transverse centerline of said absorbent article upon being partially separated from said remaining portion of said coversheet.

5. The absorbent article of claim 1, wherein said flaps are extendible in a direction substantially parallel to the longitudinal centerline of said absorbent article upon being partially separated from said remaining portion of said coversheet.

6. An absorbent article including a topsheet having a body facing surface and a garment facing surface, a backsheet joined to said garment facing surface of said topsheet, and an absorbent core positioned between said topsheet and said backsheet, said absorbent article comprising:

(a) a coversheet joined to said body facing surface of said topsheet, said coversheet including a line of weakness completely surrounding and defining a pair of flaps and a remaining portion of said coversheet at least partially surrounding said flaps, said flaps being at least partially separable from said remaining portion of said coversheet, said flaps being liquid impervious and having an exposed surface facing away from said topsheet, said flaps including a fastening adhesive on their exposed surfaces for attaching said flaps to an undergarment, and wherein said flaps may be fully separated from said remaining portion of said coversheet along line of weakness.

* * * * *

UNITED STATES PATENT AND TRADEMARK OFFICE
CERTIFICATE OF CORRECTION

PATENT NO. : 5,788,686
DATED : August 4, 1998
INVENTOR(S) : NICK A. AHR et al.

It is certified that error appears in the above-identified patent and that said Letters Patent is hereby corrected as shown below:

Column 8, line 49, after "sheet along" insert -- said --.

Signed and Sealed this

Fifteenth Day of June, 1999

Attest:

Q. TODD DICKINSON

Attesting Officer

Acting Commissioner of Patents and Trademarks